United States Patent
Semler et al.

(10) Patent No.: US 7,628,760 B2
(45) Date of Patent: Dec. 8, 2009

(54) CIRCULATION MONITORING SYSTEM AND METHOD

(75) Inventors: Herbert J. Semler, Portland, OR (US); Philip Benz, Portland, OR (US); Gary Mills, Portland, OR (US); James McNames, Portland, OR (US)

(73) Assignee: Semler Scientific, Inc., Portland, OR (US)

( * ) Notice: Subject to any disclaimer, the term of this patent is extended or adjusted under 35 U.S.C. 154(b) by 0 days.

(21) Appl. No.: 12/001,505

(22) Filed: Dec. 11, 2007

(65) Prior Publication Data
US 2009/0149764 A1    Jun. 11, 2009

Related U.S. Application Data

(60) Provisional application No. 60/904,221, filed on Feb. 28, 2007.

(51) Int. Cl.
*A61B 5/02* (2006.01)
*A61B 5/00* (2006.01)

(52) U.S. Cl. .............. 600/504; 600/309; 600/310; 600/323; 600/324

(58) Field of Classification Search ........... 600/504
See application file for complete search history.

(56) References Cited

U.S. PATENT DOCUMENTS

| 3,796,213 | A | * | 3/1974 | Stephens ............... 600/479 |
|---|---|---|---|---|
| 4,653,498 | A | * | 3/1987 | New et al. ............. 600/324 |
| 4,807,638 | A | | 2/1989 | Sramek |
| 4,830,014 | A | | 5/1989 | Goodman et al. |
| 5,337,744 | A | | 8/1994 | Branigan |
| 5,452,717 | A | | 9/1995 | Branigan et al. |
| 5,482,036 | A | | 1/1996 | Diab et al. |
| 5,490,505 | A | | 2/1996 | Diab et al. |
| 5,575,284 | A | * | 11/1996 | Athan et al. ............ 600/323 |
| 5,632,272 | A | * | 5/1997 | Diab et al. ............. 600/323 |
| 5,685,299 | A | | 11/1997 | Diab et al. |
| 5,730,138 | A | | 3/1998 | Wang |
| 5,769,785 | A | | 6/1998 | Diab et al. |
| 6,002,952 | A | | 12/1999 | Diab et al. |
| 6,036,642 | A | | 3/2000 | Diab et al. |
| 6,067,462 | A | | 5/2000 | Diab et al. |
| 6,081,735 | A | | 6/2000 | Diab et al. |
| 6,088,607 | A | | 7/2000 | Diab et al. |
| 6,157,850 | A | | 12/2000 | Diab et al. |
| 6,463,311 | B1 | | 10/2002 | Diab |

(Continued)

OTHER PUBLICATIONS

International Search Report for Int'l Application No. PCT/US2008/013592; ISA/US; Apr. 2, 2009; 10 pages.

(Continued)

*Primary Examiner*—Patricia C Mallari
(74) *Attorney, Agent, or Firm*—Ater Wynne LLP (57) ABSTRACT

A lightweight portable probe or transducer containing a transmissive or reflective electro-optical emitter and receptor in the infrared spectrum is fitted on a subject's finger or toe. Associated electronics energize and monitor the probe, detect cardio-rhythmic fluctuations therefrom, and process digital data over a prescribed window to produce a non-invasive, qualitative or quantitative measure of the subject's circulation. In accordance with one embodiment of the invention, a simple tri-color LED array is used to indicate the subject's circulation as being normal, reduced, or borderline.

15 Claims, 4 Drawing Sheets

U.S. PATENT DOCUMENTS

| | | | |
|---|---|---|---|
| 6,501,975 | B2 | 12/2002 | Diab et al. |
| 6,602,201 | B1 | 8/2003 | Hepp et al. |
| 6,650,917 | B2 | 11/2003 | Diab et al. |
| RE38,476 | E | 3/2004 | Diab et al. |
| 6,699,194 | B1 | 3/2004 | Diab et al. |
| RE38,492 | E | 4/2004 | Diab et al. |
| 6,745,060 | B2 | 6/2004 | Diab et al. |
| 6,813,511 | B2 | 11/2004 | Diab et al. |
| 6,816,741 | B2 | 11/2004 | Diab |
| 6,961,598 | B2 | 11/2005 | Diab |
| 7,044,918 | B2 | 5/2006 | Diab |
| 7,225,006 | B2 | 5/2007 | Al-Ali et al. |
| 7,239,905 | B2 | 7/2007 | Kiani-Azarbayjani et al. |
| 7,485,094 | B2 | 2/2009 | Marks et al. |
| 2002/0095077 | A1* | 7/2002 | Swedlow et al. ............ 600/323 |
| 2004/0123866 | A1 | 7/2004 | Berthon-Jones |
| 2005/0033174 | A1 | 2/2005 | Moehring et al. |
| 2005/0124901 | A1 | 6/2005 | Misczynski et al. |
| 2005/0234339 | A1 | 10/2005 | Phillips |
| 2006/0020215 | A1 | 1/2006 | Callahan, III |
| 2007/0230756 | A1 | 10/2007 | Wen et al. |

OTHER PUBLICATIONS

Radai, Michal M. et al., A Novel Telemedicine System for Monitoring Congestive Heart Failure Patients, Congestive heart failure (Greenwich, Conn., USA) 14(5):239-44, 2008.

* cited by examiner

CIRCULATION MONITORING SYSTEM AND METHOD

RELATED APPLICATIONS

This application claims the benefit of priority to U.S. patent application Ser. No. 11/014,455 titled NON-INVASIVE BODY COMPOSITION MONITOR, SYSTEM AND METHOD and filed on 20 Dec., 2004 (itself a continuation-in-part of: U.S. patent application Ser. No. 09/971,507 titled DISPOSABLE VITAL SIGNS MONITOR filed on 4 Oct. 2001, now abandoned), and U.S. Provisional application number 60/904,221, filed on 28 Feb. 2007 and entitled PERFUSION MONITOR, the disclosure contents of which are hereby incorporated herein in their entirety by this reference.

FIELD OF THE INVENTION

The invention relates generally to the field of medical monitoring. More particularly, the invention relates to circulation monitoring and indexing to indicate the merit of a subject's circulation.

BACKGROUND OF THE INVENTION

Peripheral artery disease (PAD) and related coronary heart disease (CHD) or cardiovascular disease (CVD) are potential killers.

In the US, an estimated 10 million people have PAD, with approximately the same number deemed to be undiagnosed due to lack of symptoms in approximately half of the affected population. Because of the severity of the disease endpoints (i.e. disability, limb amputation, death), easier, more accessible tools will help identify patients with PAD and diabetes at earlier stages of the disease by primary care physicians, enabling earlier intervention and avoidance of many of the disease's more severe outcomes.

PAD puts patients at elevated risk for lower extremity atherosclerosis, as well as for CHD or CVD, heart attack, stroke, and amputation. Approximately 75% of patients having PAD also have CHD or CVD. Risk of stroke is three times higher in patients with PAD than in those without the condition. PAD manifests as stenosis or obstruction of the arteries in the lower extremities and is caused by several factors including atherosclerosis, thrombosis, arterial calcification, diabetes, homocysteinemia, etc. Characterized by calf pain and disability, specifically claudication, and restricted ambulation due to critical limb ischemia, PAD is a progressive chronic disease—however, it should be noted that approximately half of all patients with PAD were free of symptoms at the time of their diagnoses.

Current diagnostic methods are typically applied to patients who present with symptoms of claudicating or leg pain at rest. A common diagnostic pathway includes use of the Ankle-Brachial Index (ABI) either at rest or during exercise, reactive hyperemia, photoplethysmography, segmental blood pressure analysis, pulse volume recording, duplex ultrasound, and peripheral angiography.

The ABI is typically the first test deployed and is usually performed in a physician's office or hospital vascular laboratory. The ABI is calculated from observations of systolic blood pressures taken from the brachial artery and at the ankle using sphygmomanometers and Doppler ultrasound. Although the ABI is considered the gold standard for non-invasive diagnosis of PAD, it is time-consuming and awkward to deploy, it is subjective, and it is technique-dependent. Thus, a relatively high and specialized training and experience level of the practitioner is required in order for consistent, reliable results to be obtained. Further, the ABI is not useful in the presence of arterial calcification, commonly encountered in patients at risk for PAD. This is because ABI relies on non-invasive blood pressure (NIBP) measurements that are confounded by arterial calcification.

Conventional photoplethysmography devices measure the volume of blood in a region of a subject's tissue. Conventional pulse oximeters measure how much oxygen binds to hemoglobin in red blood cells in a region of a subject's tissue. Neither concerns itself with a measure of quasi-periodic or cardio-rhythmic blood flow or circulation in a subject's extremity.

DETAILED DESCRIPTION OF THE PREFERRED EMBODIMENTS

Described herein are the design and mechanics of providing a "circulation index" for monitoring and indexing cardio rhythmic components in biomedical signals. Only those fluctuations in the monitored signal that are synchronous with the cardiac cycle such as arterial blood pressure, central venous pressure, and photo-plethysmograph are of interest. The index is derived from these fluctuations and is coded into a simple indicator easily read by a patient.

Data Processing Outline:

Cardiovascular signals generally contain a quasi-periodic component that is synchronous with the cardiac cycle. Although these signals are not periodic in the exact sense that $x(t)=x(t+T)$ for some period T, they share many of the properties of periodic signals. In particular, any periodic signal can be exactly represented as a sum of sinusoids, called a Fourier series, with frequencies at integer multiples of the fundamental frequency, in accordance with Equation 1:

$$f = \frac{1}{T}, \; x(t) = \sum_{k=0}^{\infty} a_k \cos(2\pi k f t + \theta_k), \quad (1)$$

In general, only a subset of this infinite sum is necessary to accurately represent the signal. Generally speaking, the smoother the signal the fewer terms that are required in the sum. Signals with abrupt events, such as the electrocardiogram (ECG) require many harmonics (up to 80), but smoother signals such as cardiovascular pressure and plethysmographic signals require only a few.

In general, it is difficult to estimate the Fourier series coefficients $a_k$ and phases $\theta_k$ because the signal is only quasi-periodic and the heart rate is unknown. A more general spectral characterization of the signal is an estimate of the power spectral density (PSD), which is a measure of how the power of the signal is distributed across a range of sinusoidal frequency components. As with all densities, the PSD is non-negative at all frequencies. In this case, the signal is essentially modeled as Equation 2:

$$x(t) = \int_0^\infty a(f)\cos[2\pi ft + \theta(f)]df, \qquad (2)$$

wherein those of skill in the art will appreciate that a(f)² is the PSD.

Quasi-periodic signals have their power concentrated at frequencies near integer multiples of the fundamental frequency, much like a Fourier series. In contrast, a signal that is lacking quasi-periodic fluctuations will typically lack power at concentrated frequencies and will instead have the power more or less equally distributed across all frequencies. Signals that contain only white noise, or uncorrelated sequences, have a PSD that is equal across all frequencies.

The spectral flatness measure (SFM) is one well-known measure of the flatness of the PSD. It is defined as the ratio of the geometric mean divided by the arithmetic mean, in accordance with Equation 3:

$$SFM = \frac{\sqrt[N]{\prod_{k=1}^{N} a(f_n)^2}}{\frac{1}{N}\sum_{k=1}^{N} a(f_n)^2}$$

The arithmetic mean is never smaller than the geometric mean, so the SFM is on a normalized scale between 0 and 1. If strong quasi-periodic components are present, then the PSD will contain power concentrated primarily at a few frequencies and the SFM will be close to 0. If the signal only contains white noise, the PSD will be flat and the SFM will be close to 1. Although the SFM is normally defined over the entire frequency range of the PSD, it can also be applied to any band of frequencies.

The circulation index is a measure of how strong the quasi-periodic component of the signal, which is essentially the opposite of what the SFM estimates. Thus, the circulation index is defined in accordance with Equation 4:

$$CI = 1 - SFM \qquad (4),$$

wherein the SFM is computed over a frequency range that covers the lowest expected heart rate (≈0.75 Hz) and the highest expected harmonic of the heart rate in a photo-plethysmographic signal (≈20 Hz). Like the SFM, this is on a normalized scale of 0 to 1, though it is normally expressed as a percentage. Although SFM has been used in speech processing and other applications, it has never before been applied to cardiovascular signals.

In practice, the PSD cannot be computed directly from a signal because it requires that the entire signal be observed. Instead the PSD must be estimated from a finite segment, typically with a sliding window approach. Those of skill in the art will appreciate that, within the spirit and scope of the invention, there are many methods to estimate the PSD, both parametric and nonparametric.

The invented method thus can be briefly summarized as follows:

a. Light-dark fluctuations with a period characteristic of cardiac cycle are received by a photodetector.
b. The fluctuations are analog-filtered and converted via an analog-to-digital converter (ADC) to digital data.
c. The data are "windowed", i.e. the most recent n (e.g. 8) seconds of data are "entered" into a dynamic data buffer and digitally filtered.
d. Calculations are performed on the data in the data buffer. The windowed data are analyzed to: i) remove the background "steady-state" light effect to isolate only the time-varying elements of the light-dark fluctuation; ii) "estimate" the power spectral density (PSD) for that n-second window; iii) calculate a spectral flatness measure (SFM) for that PSD data; and iv) subtract the SFM from 1.0 to determine the value called the circulation index (CI) for the n-second window.

The analysis of the received light-dark fluctuation values reduces "noise", i.e. optical signal unrelated to the cardiac cycle elements of this light-dark fluctuations and enhances discrimination of the signal arising from the cardiac cycle elements of the light-dark fluctuations in the monitored area of the subject's extremity. The change in this signal, i.e. the CI, varies with the degree of circulation.

Those of skill in the art will appreciate that the CI is a dynamic measurement for each subject. As with blood pressure, CI thresholds indicative of physical hemodynamics are empirically based on observation of subjects: 120/80 can mean different things for different people (e.g. 120/80=pulse pressure of 40 and 160/120=pulse pressure of 40). Unlike NIBP, CI observations are more stable from one observation on a subject to the next.

Thus, the invention involves a new method and apparatus for the non-invasive assessment of peripheral artery disease (PAD) and/or related coronary heart disease (CHD) or cardiovascular disease (CVD) using a non-invasive circulation monitor and deriving from characteristics of light transmitted through a person's extremity, e.g. a finger or toe, a circulation index to visually annunciate whether and to what extent the person has PAD and/or CHD or CVD.

Figure 1:
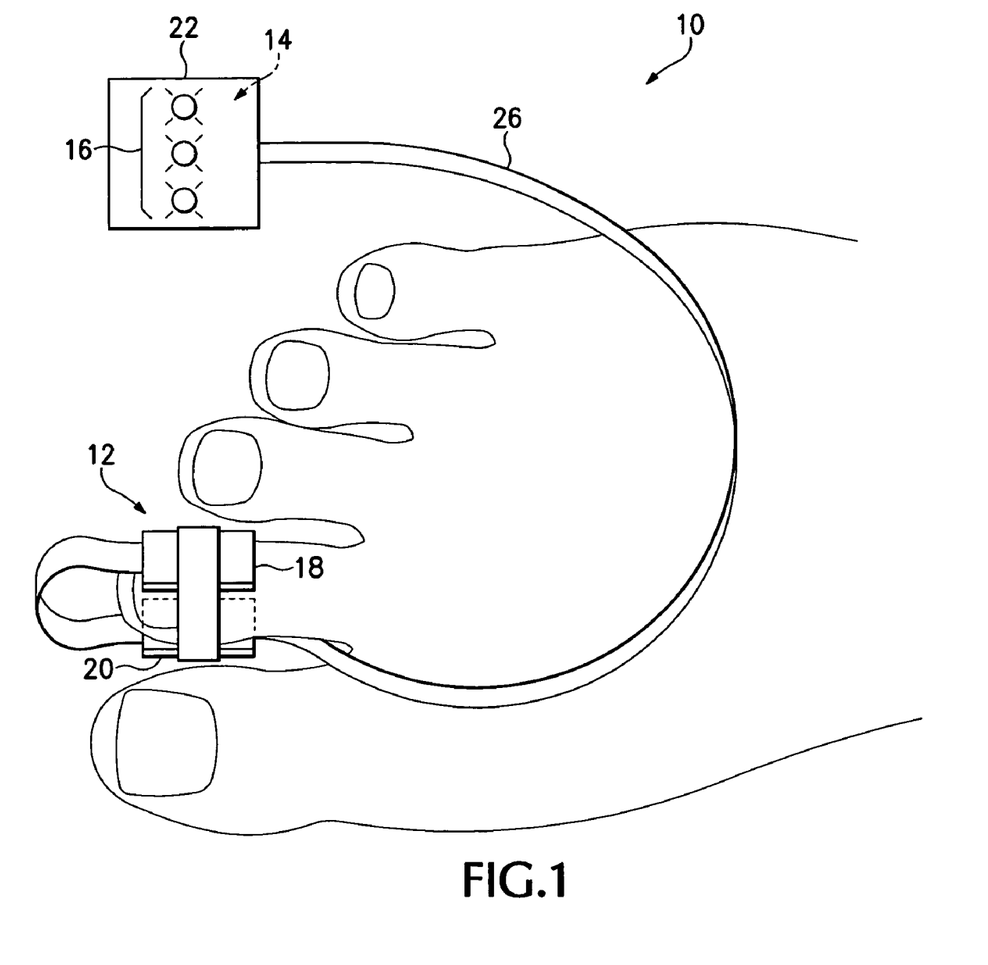
FIG. 1 is an isometric view of the invented device in accordance with one embodiment of the invention.

FIG. 1 is an isometric view of invented apparatus or system 10 in accordance with one embodiment of the invention. FIG. 1 shows apparatus 10 as including a finger or toe "probe" or transducer 12 operatively coupled with a nearby processor 14 and a nearby indicator 16. Those of skill in the art will appreciate that probe 12 includes a photo emitter, e.g. an infrared (IR) light source 18 and a photo receptor, e.g. an IR light receptor 20, the two cooperating to illuminate a region of a subject's extremity, e.g. a hand, foot, finger, thumb or toe, and to sense the transmitted or reflected light energy responsive to biomedical fluctuations in the extremity. Those of skill will appreciate that one such biomedical fluctuation represents cardio-rhythmic flow, referred to herein simply as circulation, through the subject's extremity.

In accordance with one embodiment of the invention, the light emitted by photo emitter 18 is characterized by a single wavelength of light. Those skilled in the art will appreciate that such single wavelength operation of emitter 18 and respondent receptor 20 renders apparatus 10 less expensive and lighter in weight. Alternatively, however, and yet within the spirit and scope of the invention, multiple wavelengths of light may be used.

Those of skill in the art will appreciate that processor 14 and indicator 16 can be integrated into a housing that also encompasses probe 12, or that such can be separately integrated into a remote housing 22, as indicated. Processor 14 and any attendant circuitry such as batteries, memory, and peripheral signal driving/receiving/conditioning circuitry will be described in more detail below by reference to FIG. 2. Indicator 16 will be understood in accordance with one embodiment of the invention to include one or more light emitting diodes (LEDs), e.g. three color-differentiated LEDs, that indicate to the subject or a clinician one condition chosen from a group consisting of normal, reduced and insignificant circulation in the extremity. Those of skill will appreciate that alternative display technologies (e.g. a liquid crystal display (LCD), an organic light emitting diode (OLED) micro-reflector, etc. giving a graphical rendering of the windowed data or the circulation index derived therefrom) are contemplated as being within the spirit and scope of the invention.

Those of skill also will appreciate that housing 22 can include other circuitry, e.g. buffered window data recording memory, and one or more external communication ports, e.g. a USB port for conveying recorded data to a nearby or remote location for oversight and archival purposes.

In accordance with FIG. 1, illustrated probe 12 operates transitively, with photo emitter 18 and photo receptor 20 on opposite sides of the extremity, e.g. the finger or toe. Alternatively, probe 12 can operate reflectively, with photo emitter 18 and photo receptor 20 on the same side of the extremity and with a reflective medium such as a mirror on the opposite side thereof or simply by reflection off the bone and tissue. Either alternative configuration is contemplated as being within the spirit and scope of the invention.

Those of skill in the art will appreciate that probe 12 can take alternative physical forms. For example, probe 12 can take the form of a flexible expanse not unlike an adhesive band aid that surrounds or substantially surrounds the finger or toe. (Such can be done in accordance with the teachings of the above-referenced body composition monitor patent application.) Or it can take the form of a rigid integrally formed band or ring that slips over or around and partially or completely encircles the end of the finger or toe, or a rigid integrally formed thimble-like cap that slips over the end of the finger or toe. Or it can take the form of a rigid formed and assembled spring clip that gently pinches the finger or toe. All such embodiments and other suitable alternatives are contemplated as being within the spirit and scope of the invention. For subjects who are missing fingers and/or toes, e.g. diabetics, amputees, etc., probe 12 can take a suitable alternative form capable of illuminating and monitoring light/dark fluctuations in the subject's extremity, e.g. a hand or foot.

Figure 2:
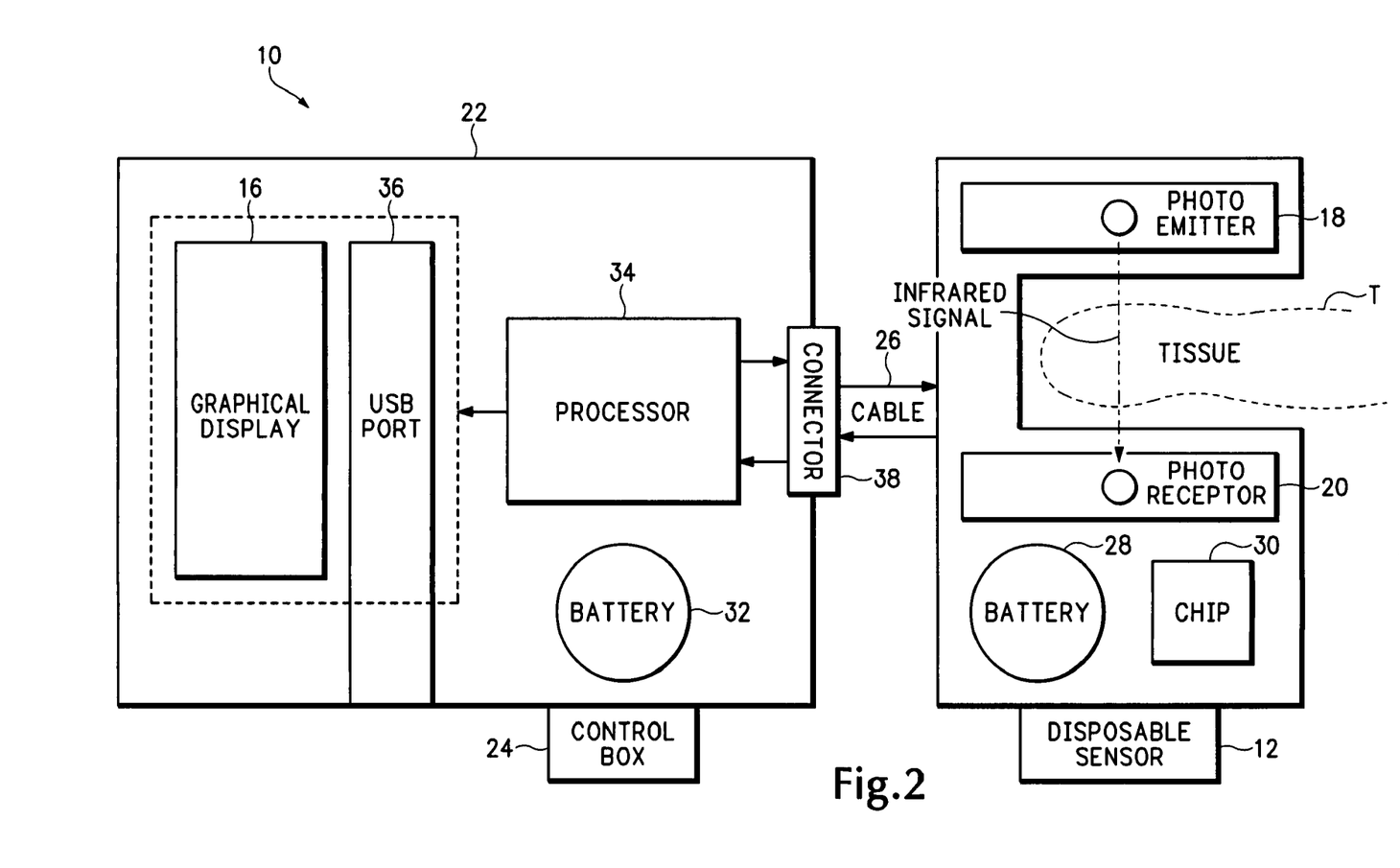
FIG. 2 is a schematic diagram of the invented device shown in FIG. 1.

FIG. 2 is a schematic diagram of invented apparatus or system 10 shown in FIG. 1. FIG. 2 shows disposable probe or sensor 12 and control box or circuitry 24 in housing 22 interconnected via a flexible signal wiring harness or cable 26. Sensor 12 includes a battery 28, an electronic chip 30, infrared photo emitter 18 and infrared photo receptor 20 with a subject's finger or toe tissue T extending therebetween in a transmissive configuration. Control circuitry 24 includes a battery 32, a processor 34, a USB port 36, a graphic display or indicator 16, and a connector 38. Those of skill in the art will appreciate that chip 30 transmits, receives and conditions signals to/from photo emitter 18 and photo receptor 20, and is powered by battery 28. Those of skill in the art will also appreciate that processor 34 commands and processes responsive signals to and from chip 30, converts the signals to windowed cardio-rhythmic fluctuation data over a determined window of time, compares the level of such cardio-rhythmic data to defined threshold data, and drives graphic display or indicator 16 to indicate what is referred to herein as a circulation index, or coded indication of normal (good), reduced (bad) or insignificant (borderline) circulation. The debited analog and digital signal monitoring and processing technique will be described below by reference to FIG. 3. Thus, from this description and the figures, one having skill in the art will understand that an embodiment of a circulation monitoring apparatus comprises a transducer configured to illuminate and monitor light fluctuations through tissue within an anatomical extremity to produce a signal indicative of the fluctuations, the transducer including a photo emitter for emitting a light signal to illuminate the extremity and a photo receptor for receiving a light signal responsive thereto, a processor operatively coupled with the transducer, the processor configured to analyze the signal for periodicity and to measure the signal for amplitude, a comparator operatively coupled with the processor, the comparator configured to compare the measured amplitude of the signal to one or more predefined threshold amplitudes, and an indicator operatively coupled with the comparator, the indicator configured to indicate a circulation level from the comparator.

Figure 3:
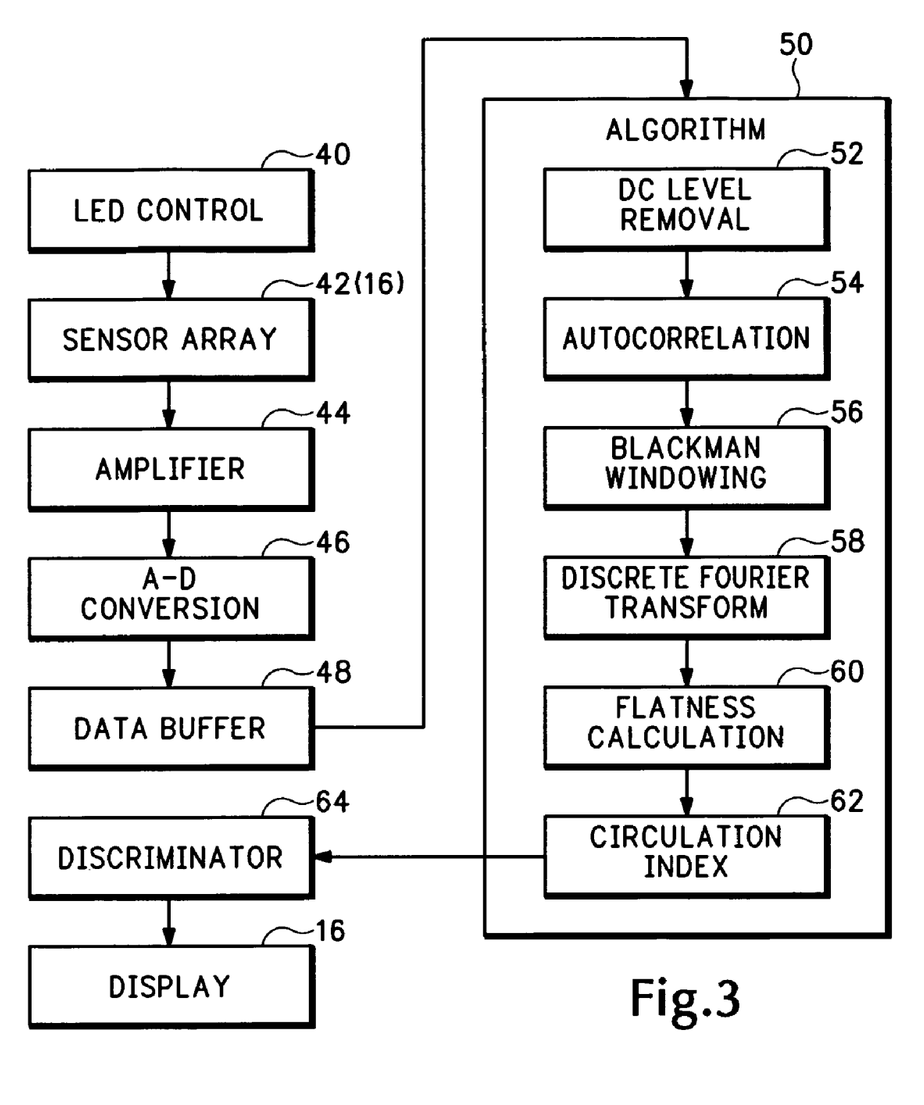
FIG. 3 is a process flow diagram illustrating the invented circulation monitoring method.

FIG. 3 is a process flow diagram illustrating the invented circulation monitoring method, and is best understood in light of the Data Processing Outline above.

FIG. 3 shows an LED (IR) control 40, which drives a(n IR) sensor array 42 (referred to more simply herein as photo receptor 20), which drives an amplifier 44, which drives an analog-to-digital (A-D) converter 46, which drives a data buffer 48 that buffers sufficient data to feed the digital signal processing (DSP) software 50 executed by processor 34 (refer briefly back to FIG. 2). Within software 50, a DC level removal step 52; an auto-correlation step 54; a windowing, e.g. Blackman windowing because of its selectivity and sharp roll-off or edges, step 56; a DFT-shifting step 58; a flatness calculation step 60; and a circulation index calculation step 62 are performed by executing instructions stored within a memory either within processor 34 or external thereto. The circulation index is discriminated against or compared at 64 with stored categorical (contiguous interval) threshold levels, as described below, and a qualitative (e.g. good/bad/in-between) or quantitative (85%) measure of the subject's circulation is displayed at display 16 (refer briefly back to FIG. 2.)

Those of skill will appreciate that certain illustrated functional blocks can be omitted, reordered, combined, or separated, within the spirit and scope of the invention. Similarly, those of skill will appreciate that certain illustrated software steps can be omitted, reordered, combined, or separated, also within the spirit and scope of the invention. All such suitable topologically and logically suitable alternatives to the process flow diagramed in FIG. 3 are contemplated as being within the spirit and scope of the invention.

Figure 4:
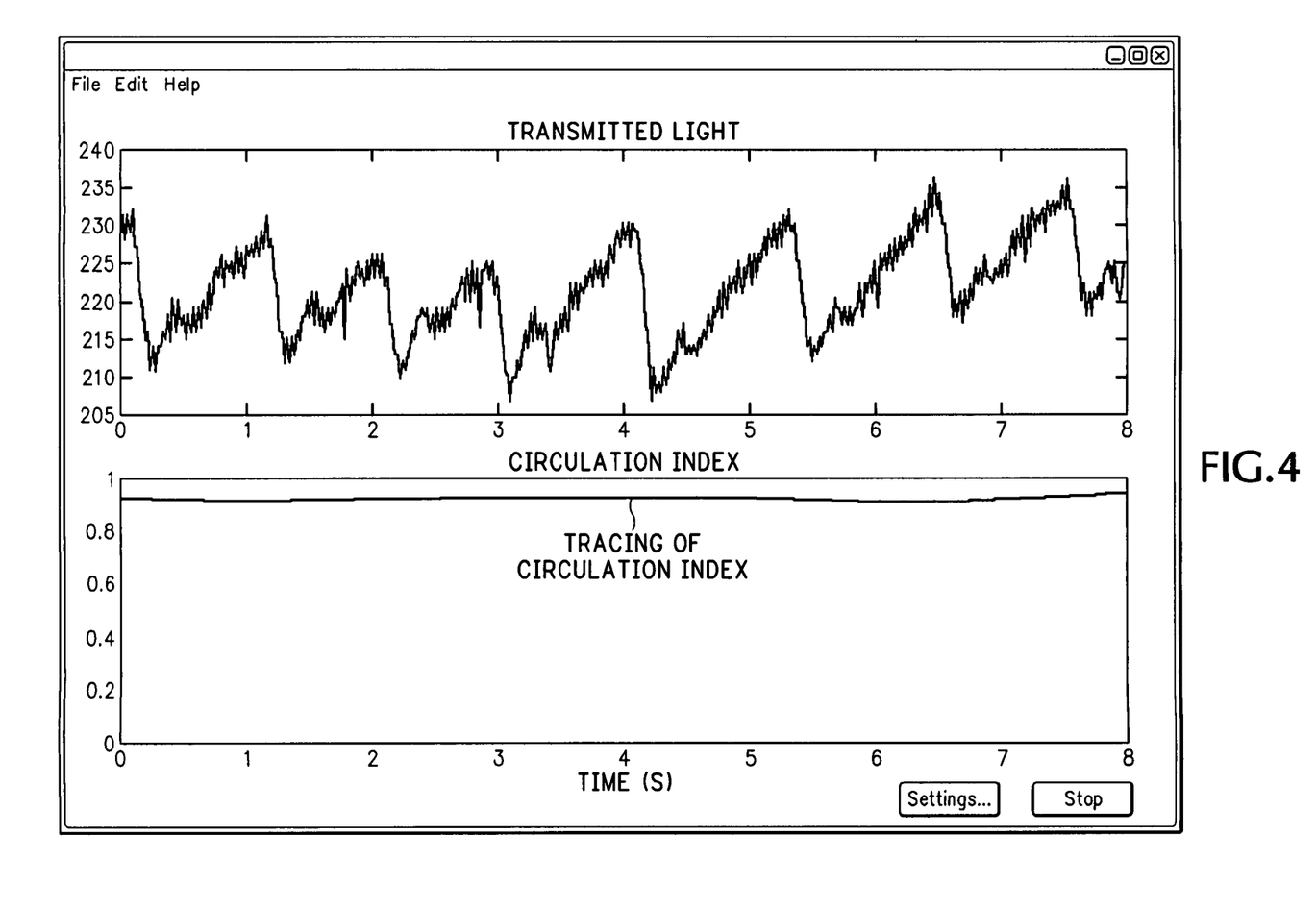
FIG. 4 is a graph of a typical circulation index derived from the invented circulation monitoring method.

FIG. 4 is a graph of a typical circulation index derived from the invented circulation monitoring method. The upper trace of FIG. 4 shows the transmitted or reflected light detected by the photo detector over a window of time, while the lower trace of FIG. 4 shows the derived circulation index over the same window of time (mapped into contiguous intervals and based upon power spectral density distributions of data from the transmitted light measurements). Those of skill in the art will appreciate that FIG. 4 features a subject with good circulation, as the circulation index is consistently $\geq 0.9$ on a scale from 0.0 to 1.0. Subjects with PAD and/or CHD or CVD would have far lower circulation indices. As suggested by FIG. 4, transmitted light waveform and circulation index data can be recorded and optionally uploaded to a clinician for outplay, review, and/or archiving. Such can be done in accordance with the invention by any suitable means such as wired or wireless conveyances including telephone, cable, Internet, and the like.

In accordance with one embodiment of the invention, normal (represented by a green light) is defined by a circulation index (CI)$\geq 0.8$; reduced (represented by a yellow light) is defined by a $0.5 \leq CI \leq 0.79$; and insignificant (represented by a red light) is defined by a CI$\leq 0.49$. Those of skill in the art will appreciate that, within the spirit and scope of the invention, these thresholds can be set differently. It is believed that reduced or insignificant circulation indices indicate moderate to severe PAD.

Experiment:

Objective:

The objective was to develop a simple, safe, accurate bedside monitor to detect circulation in patients with PAD (and possibly also CHD or CVD).

Methodology:

A custom optical probe that measures infrared light transmission through a finger or toe has been developed. The invented hand-held device was fitted to the left and right second toe of twenty patients having PAD (mean age 72 years) and 20 age-matched healthy subjects (mean age 69 years).

The self-contained probe detected a degree of circulation in three levels which were indicated by color coded LED's. Green indicated good circulation; yellow indicated reduced or borderline circulation; and red indicated insignificant circulation. The measurements were compared to the ankle brachial index (ABI) by an independent vascular specialist prior to the use of the test device. In other words, the gold-standard but difficult-to-use-and-interpret ABI was used to calibrate the invented apparatus and system.

Results:

Of the patients with PAD, seventeen had insignificant circulation, and two had borderline circulation. All twenty of the healthy subjects showed good circulation. Sensitivity of the device was 87.8% and the specificity of the device was 100%. Thus, false negative PAD diagnoses were few or none and false positive PAD diagnoses were non-existent using the invented system and method.

Conclusions:

The new lightweight, portable monitor for monitoring and indexing circulation is an accurate, objective means of distinguishing patients with PAD and normal age-matched subjects. The portable, lightweight and optionally disposable probe is simply (requires no additional apparatus, e.g. auscultatory or other non-invasive blood pressure (NIBP), Doppler, cuffs, gels, etc.), quickly (deployment takes less than three minutes) fitted, and yet it can provide an integral or remote visual indicator of peripheral circulation. It has the potential to be a non-invasive screening test for PAD, suitable for outpatient or in-home assessment. Use of the invention is warranted and could improve patient self-monitoring and compliance, and demonstrably can delay progression of PAD by its early detection.

This is because PAD is a very important risk factor for identifying coronary artery disease and cerebrovascular disease, as they share common risk factors and pathogenesis. A simple non-invasive test for peripheral vascular disease would identify PAD candidates, and would also serve as a beacon for potential co-existing coronary artery disease and cerebrovascular disease. Its recognition would allow early intervention with preventive measures such as diet, exercise, eliminating tobacco, medications and, if necessary, possible revascularization procedures for saving limbs and lives.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope, of the invention.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

Finally, those of skill in the art will appreciate that the invented method, system and apparatus described and illustrated herein may be implemented in software, firmware or hardware, or any suitable combination thereof. Preferably, the method system and apparatus are implemented in a combination of the three, for purposes of low cost and flexibility. Thus, those of skill in the art will appreciate that embodiments of the methods and system of the invention may be implemented by a computer or microprocessor process in which instructions are executed, the instructions being stored for execution on a computer-readable medium and being executed by any suitable instruction processor.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

We claim:

1. Circulation monitoring apparatus comprising:
    a transducer configured to illuminate and monitor light fluctuations through tissue within an anatomical extremity to produce a signal indicative of the fluctuations, the transducer including a photo emitter for emitting a light signal to illuminate the extremity and a photo receptor for receiving a light signal responsive thereto;
    a processor operatively coupled with the transducer, the processor configured to analyze the signal for periodicity and to measure the signal for amplitude, wherein the processor executes memory-based instructions including:
        instructions for DC level component removal from the signal;
        instructions for auto-correlating the signal;
        instructions for windowing the signal;
        instructions for producing a discrete Fourier transform (DFT) of the signal; and
        instructions for calculating the spectral flatness measure (SFM) of the signal;
    a comparator operatively coupled with the processor, the comparator configured to compare the measured amplitude of the signal to one or more predefined threshold amplitudes; and
    an indicator operatively coupled with the comparator, the indicator configured to indicate a circulation level from the comparator.

2. The apparatus of claim 1, wherein the indicator includes a tri-color light array indicating three levels of comparison.

3. The apparatus of claim 2, wherein the tri-color light array indicates normal, reduced and insignificant circulation in the extremity.

4. The apparatus of claim 1, wherein the transducer includes an extremity-embracing circumferential expanse.

5. The apparatus of claim 4, wherein the expanse is flexible.

6. The apparatus of claim 1, wherein the transducer operates reflectively from one side of the extremity.

7. The apparatus of claim 1, wherein the transducer includes an adherent one-sided extremity-contacting expanse.

8. The apparatus of claim 2, wherein the processor, the comparator, and the indicator operate digitally, the apparatus further comprising:
    an analog-to-digital converter operatively coupled between the transducer and the processor.

9. The apparatus of claim 8, wherein the transducer, the converter, and the processor operate collectively to capture a window of time-based signal amplitude data representing cardiac rhythmic circulation indicia.

10. The apparatus of claim 1 further comprising:
either of a flexible wiring harness or a cable extending between the transducer and the processor.

11. The apparatus of claim 10 further comprising:
a housing at an end of either of the cable or the wiring harness opposite the transducer, the housing configured to contain the processor, the comparator, and the indicator.

12. The apparatus of claim 1, wherein the windowing instructions perform Blackman windowing.

13. The apparatus of claim 1, wherein the transducer is disposable.

14. The apparatus of claim 1 further comprising:
a communications port for operatively coupling with and conveying signal information to an auxiliary device.

15. The apparatus of claim 1, wherein the photo emitter operation is characterized by a single wavelength of light.

* * * * *

UNITED STATES PATENT AND TRADEMARK OFFICE
CERTIFICATE OF CORRECTION

| | |
|---|---|
| PATENT NO. | : 7,628,760 B2 |
| APPLICATION NO. | : 12/001505 |
| DATED | : December 8, 2009 |
| INVENTOR(S) | : Herbert J. Semler et al. |

Page 1 of 1

It is certified that error appears in the above-identified patent and that said Letters Patent is hereby corrected as shown below:

Column 1, line 6, after "This application" insert --is a continuation-in-part of and--.

Column 1, line 7, "11/014,455" should read --11/017,455--.

Signed and Sealed this

Second Day of March, 2010

David J. Kappos
*Director of the United States Patent and Trademark Office*